United States Patent
Lee et al.

(10) Patent No.: US 6,291,726 B1
(45) Date of Patent: Sep. 18, 2001

(54) PROCESS FOR NITRATION OF AROMATIC COMPOUNDS USING A NON-ACID TYPE NITRATION PROCESS

(75) Inventors: Bon-Su Lee; Kyoo-Hyun Chung, both of Inchon; Yoon-Sik Lee; Young-Gyu Kim, both of Seoul, all of (KR)

(73) Assignee: Inha University Foundation, Inchon (KR)

( * ) Notice: Subject to any disclaimer, the term of this patent is extended or adjusted under 35 U.S.C. 154(b) by 0 days.

(21) Appl. No.: 09/622,285

(22) PCT Filed: Sep. 18, 1998

(86) PCT No.: PCT/KR98/00285

§ 371 Date: Oct. 18, 2000

§ 102(e) Date: Oct. 18, 2000

(87) PCT Pub. No.: WO99/42433

PCT Pub. Date: Aug. 26, 1999

(30) Foreign Application Priority Data

Feb. 18, 1998 (KR) .................................................. 98-5014

(51) Int. Cl.⁷ .................................................. C07C 205/00
(52) U.S. Cl. .......................... 568/939; 568/940; 568/932; 568/934
(58) Field of Search ..................... 568/939, 940, 568/932, 934

(56) References Cited

U.S. PATENT DOCUMENTS

| | | |
|---|---|---|
| 4,104,145 | 8/1978 | Ando et al. . |
| 4,426,543 | 1/1984 | Schumacher et al. . |
| 4,820,859 | 4/1989 | Millar et al. . |

FOREIGN PATENT DOCUMENTS

| | | |
|---|---|---|
| 0497989 | 8/1992 | (EP) . |
| A131982 | 10/1919 | (GB) . |

OTHER PUBLICATIONS

Suzuki et al., Chemistry Letters, pp. 1421–1424, 1993.
Imanishi et al., J. Chem. Soc., Chem. Commun., 1991.
Millar et al., Chapter 11, Novel Syntheses of Energetic Materials Using Dinitrogen Pentoxide, 1996.
Quakenbush & Pennington, Chapter 19, Commercial Dinitrotoluence Process, 1996.
Suzuki et al., J. Chem. Soc., Perkimn Trans. 1, pp. 2358–89 (1996).
Akolekar et al., Res. Chem. Intermed., vol. 1, No. 1, pp. 7–16 (1995).

*Primary Examiner*—Samuel Barts
(74) *Attorney, Agent, or Firm*—Birch, Stewart, Kolasch & Birch, LLP

(57) ABSTRACT

The nitration of aromatic compounds is achieved in high yield and selectivity by using oxygen activated by an inorganic catalyst and nitrogen dioxide. Since this process uses neither concentration nitric nor sulfuric acids, the generation of spent waste acid does not occur. Furthermore, the process does not encounter the problem of high costs associated with the generation of ozone as in an alternative nitration process. Since the solubility of oxygen in a reaction medium is increased by using pressurized oxygen, nitrogen dioxide is activated by a porous inorganic oxide and thus an aromatic compound(e.g., benzene) is nitrated into a nitro compound (e.g., PhNO2), the reaction rate is significantly increased, and the recovery of reactants is easy due to the insolubility of the catalyst.

10 Claims, No Drawings

PROCESS FOR NITRATION OF AROMATIC COMPOUNDS USING A NON-ACID TYPE NITRATION PROCESS

This application is the national phase under 35 U.S.C. § 371 of PCT International Application No. PCT/KR98/00285 which has an International filing date of Sep. 18, 1998, which designated the United States of America.

BACKGROUND OF THE INVENTION (a) Field of the Invention

The present invention relates to a process for the nitration of aromatic compounds, and more particularly to a process for the nitration of aromatic compounds through a nitration process which does not use mixed acids or nitric acid as the nitrating agent.

(b) Description of the Prior Art

Aromatic nitro compounds produced through a nitration process are widely used as starting materials for the production of, or the intermediate products for, a variety of agro-chemicals, pharmaceuticals, dyes, explosives, and rubber chemicals. Among the different aromatic nitro compounds, nitrobenzene and dinitrotoluene are of great importance as starting materials for MDI(Methylene Diphenyl Isocyanate) and TDI(Toluene Diisocyanate), respectively.

A mixed acid containing concentrated nitric acid and concentrated sulfuric acid is presently used in the nitration of aromatic compounds (see Euler, H. *Ann. Chem.*, 330, 280(1903)). When such a mixed acid is used in the nitration process, a large amount of waste sulfuric acid is produced as a by-product, of which treatment is a burden to the industry. Further, the resulting waste water, including the water used for the cleaning process, is a dire environmental problem that needs to be solved.

In an effort to solve these problems, it is reported that Olin corporation of USA has recently developed a nitration process that can effectively convert toluene into dinitrotoluene using concentrated nitric acid only but not using sulfuric acid (see Quakenbush A. B. and Pennington B. T., *ACS Symposium Series* 623, American Chemical Soc., Washington. D.C. 1996, pp 214–222). However, a separate process is needed in this method to maintain a high concentration of nitric acid in order to prevent a reduction in reactivity by the water produced as a by-product during the nitration process. Also, as it is not easy to control the reactivity of the nitration process, additional trinitrotoluene is produced by the continuing reaction. Moreover, the problem of waste water remains, and the separation of the final products after the completion of the reaction is not an easy task.

Although another nitration process has been developed in which dinitrogen pentoxide in an organic solvent is used, it is difficult to apply the process for commercial purposes because an efficient process for preparing dinitrogen pentoxide has yet to be established. (see Millar R. W. et al., *ACS Symposium Series* 623, American Chemical Soc., Washington. D.C., 1996, pp 104–121; Millar R. W. et al., U.S. Pat. No, 4,820,859 (1989)).

Suzuki et al. disclosed a nitration process which can be easily carried out in an organic solvent by using gaseous nitrogen dioxide and an oxidant, ozone(see Suzuki H., et al., *Chem. Letters*, 1421(1993); Suzuki H., et al., *J.C.S. Chem Commun*, 1409(1991); EPO 497 989 A1, 1991). This process can solve the above stated problem occurring in the conventional processes using mixed acid. Further, Korean Patent Application No. 95-32526 filed by the inventor of the present patent application discloses a process which can effectively carry out a nitration process by using nitrogen dioxide and ozone in the presence of nitric acid. However, since ozone used as an oxidant during the nitration reaction can only be obtained by discharging oxygen at a high voltage, an expensive ozone generator and large amounts of electricity are needed for the mass production of ozone. Accordingly, this process has feasibility problems with regard to an industrial application.

Further, Suzuki et al. also discloses a nitration process which uses dichloroethane(EDC, ethylene dichloride) as a solvent and use no ozone but oxygen in the presence of catalysts such as $Fe(acac)_3$ (see Suzuki H., et al., to *J.C.S. Perkin Trans.*, 1, 2358(1996)). However, a long reaction time (e.g. 12 to 36 hours) is needed in this process even though large amounts of nitrogen dioxide (31 equivalent) and a catalyst (10 mol %) are used. Further, if the reaction is conducted without the use of an additional solvent, the reaction is slow. Thus, the nitration process using nitrogen dioxide and oxygen has low reactivity and can not be a substitute for the conventional commercial nitration processes. Akolekar et al. have reported that nitration of toluene using nitrogen dioxide was possible on zeolite catalysts such as H-ZSM-5, H-modernite, and HY. (see Akolekar D. B., et al., *Res. Chem. Interm.* 21, 7 (1995)). However, total conversion was not over 60% even though excess nitrogen dioxide (8–10 equivalent) was used under very high pressure (2,430 psi) and temperature (110° C.). Moreover, Sato et al. have disclosed vapor-phase processes for the nitration of benzene with nitrogen dioxide or nitric acid in the presence of catalyst of acidic mixed metal oxides. (see U.S. Pat. No. 4,551,568 (1985), U.S. Pat. No. 5,004,846 (1990), U.S. Pat. No. 5,030,776 (1991)).

The inventors of the present invention have developed a nitration process using nitrogen dioxide and an inorganic salt type catalyst (Korean Patent Application No. 97-27617). According to the process, nitrogen dioxide is activated and aromatic compounds are effectively nitrated by pressurized oxygen without using an additional solvent. However, in this process, since an inorganic salt type catalyst such as ferric chloride can be converted into an organometal type catalyst by reacting with nitrogen dioxide and nitric acid produced during the process, and the solubility of the catalyst in the reaction mixture increases, it is difficult to recover the catalysts by simple filtration after the reaction. Thus, significant amount of the catalyst dissolved in the reaction mixture must be removed by washing with water.

SUMMARY OF THE INVENTION

It is therefore an object of the present invention to provide a process for the nitration of aromatic compounds which does not use mixed acids or nitric no acid such that spent acid generated after the reaction, does not need to be processed.

It is another object of the present invention to provide a process for the nitration of aromatic compounds which has a good reactivity and the products are easy to be separated and purified.

DETAILED DESCRIPTION OF THE INVENTION

The present invention discloses a process of adding nitrogen dioxide and oxygen to an aromatic compound, and conducting a nitration or dinitration reaction by using an inorganic oxide catalyst with a surface area of 100 $m^2/g$ or more and a micro pore size of 5 Å or more.

During the process of the present invention, if the reaction temperature is suitably raised and a sufficient amount of nitrogen dioxide is used, a mononitro compound generated, as a first compound by nitration, is maintained in a liquid state, then converted into a dinitro compound. The oxygen pressure in reaction mixture need to be maintained above 1 atm depending on the substrates, more specifically at about 3 to 8 atm in case of benzene or toluene, in order to increase the solubility of oxygen in the reactor.

After the completion of the reaction, a nitric acid by-product is separated and removed by adding water after the used catalyst is filtrated. Since the catalyst is insoluble in organic solvents, it is easy to separate the catalyst from the reaction mixture, then remove and recover all of the same after the completion of the reaction.

The mononitration or dinitration reaction of the present invention is carried out in an aromatic solvent which functions as a reactant as well.

Hereinafter, though the present invention will be described in greater detail with reference to examples, the examples are not intended to limit the scope of the invention.

According to the present invention, the nitration of aromatic compounds is carried out by using only nitrogen dioxide, oxygen and catalysts. Specifically the process for the nitration of aromatic compounds in accordance with the present invention comprises: charging a high pressure reactor such as an autoclave with an aromatic compound into; adding nitrogen dioxide; feeding oxygen in the presence of an inorganic oxide catalyst having a surface area of 100 m$^2$/g or more and a micropore mouth size of 5 Å or more, and conducting a nitration reaction with pressure to form a reaction mixture; filtrating the used catalyst from the reaction mixture and recovering the same; and adding water to remove nitric acid formed as a by-product by layer-separation.

The catalyst preferably has a micropore mouth size of 5 Å or more; because this is the size of the aromatic compound molecules, thereby enabling the aromatic compound to enter the mouth of the micropore and be absorbed on and absorbed from the catalyst. If the size of the aromatic compound molecules is larger than the size of the mouth of the micropore, the compound can not enter the micropore, nor can the molecules formed within the micropore withdraw from the same. Further, the catalyst preferably has a surface area of 100 m$^2$/g or more. The surface area of a catalyst is typically the sum of areas of walls of a micropore, and the size of a micropore is in inverse proportion to the surface area of a catalyst. Hence, the catalyst of the present invention should preferably satisfy both the above conditions of having micropore mouth size of 5 Å or more and a surface area of 100 m$^2$/g or more. Catalysts fulfilling the two conditions include silica gel, γ-alumina, magnesium silicate, Zeolite, Kaoline, silicious earth. For the Zeolite, MCM (meso-porous zeolite), sodium mordenite, NaY and others are preferable, while Kieselguhr is not. Moreover, Zeolite X or Y is better than Zeolite A as Zeolite A has micropores of 8 oxygen atoms, while Zeolite X or Y has micropores of 12 oxygen and, thus, can easily absorb large molecules.

Further, for the catalyst, it is possible to use an inorganic oxide catalyst containing metal ions such as iron ion, copper ion, cobalt ion and others. In one embodiment of the invention, to prepare such a catalyst, ferric chloride is dissolved in a solvent, and refluxed with an inorganic oxide catalyst such as silica gel. The solution is then filtrated, washed and aged at a high temperature.

Moreover. since the catalysts used in the present invention are insoluble in organic solvents, they are not dissolved in the reaction mixture of the nitration reaction. Accordingly, all of the catalysts can be effectively recovered by filtration after completion of the reaction.

The suitable level of partial pressure of oxygen varies according to the reactivity of the aromatic compounds and the oxygen is activated while being pressurized by the catalysts. The activated oxygen converts nitrogen dioxide of no reactivity into an activated form, so that it functions to transfer nitro group to the aromatic compounds absorbed on the surface of the catalyst. The pressurized oxygen is easily dissolved in the reaction mixture, contacted sufficiently with the metal catalyst introduced to activate oxygen, so that the reactivity of nitration reaction is improved. The more the presence of activated oxygen, the more nitrogen dioxide is oxidized. thereby promoting nitration.

The inside of the reactor is pressurized to a predetermined level, the pressurization time being adjusted according to the reaction time.

Further, it is possible to run the nitration reactions in the absence of solvents inside the reactor, under which condition, the aromatic compound functions as both the reactant and the solvent concurrently. In this way, the reactivity of nitration is improved and post-treatment process can be simplified.

DESCRIPTION OF THE PREFERRED EMBODIMENT

The present invention will be illustrated in greater detail by way of the following examples. The examples are given for illustration of the invention and are not intended to be limiting thereof.

EXAMPLE 1

After supplying 0.1 mol of benzene to an autoclave, also added to the same were 2.0 g of silica gel (70–230 mesh, for column chromatography) having a surface area of more than 100 m$^2$/g and a micropore of 5 Å or more and 0.2 mol of liquid nitrogen dioxide. Oxygen was injected into the autoclave at a pressure of 40 psi and then the reactants were reacted at 45° C. for 1.5 hours while the same level of pressure was maintained. After the completion of the reaction, analysis by gas chromatography revealed the obtainment of nitrobenzene at a yield of more than 99%.

EXAMPLE 2

The same procedure as described in Example 1 was carried out, except that silica gel (14–20 mesh, for desiccant) was used as a catalyst. As a result, nitrobenzene was obtained at a yield of more than 99%. Also, reactivity and efficiency of nitration reaction were maintained at levels identical to those in Example 1.

EXAMPLE 3

The same procedure as described in Example 2 was carried out, except that 1.0 g of catalyst was used. As a result, nitrobenzene was obtained at a yield of more than 99%.

EXAMPLE 4

0.1 mol of benzene, 2 g of silica gel (14–20 mesh) and 0.15 mol of liquid nitrogen dioxide were poured into an autoclave. Next, oxygen was injected at a pressure of 40 psi and then the reactants were reacted at 45° C. for 3.0 hours while the same level of pressure was maintained. After the completion of the reaction, analysis by gas chromatography revealed the obtainment of nitrobenzene at a yield of more than 96%.

EXAMPLE 5

0.1 mol of benzene, 2 g of silica gel (14–20 mesh) and 0.1 mol of liquid nitrogen dioxide were poured into an autoclave. Next, oxygen was injected at a pressure of 40 psi and then the reactants were reacted at 45° C. for 2.0 hours while the same level of pressure was maintained. After the completion of the reaction, analysis by gas chromatography revealed the obtainment of nitrobenzene at a yield of more than 65%.

EXAMPLE 6

The same procedure as described in Example 1 was carried out, except that γ-alumina (70–230 mesh, for column chromatography) having a surface area of more than 400–500 m$^2$/g and a micropore size of 5 Å or more as a catalyst was used. As a result, nitrobenzene at a yield of more than 99% was obtained.

EXAMPLE 7

The same procedure as described in Example 1 was carried out, except that magnesium silicate (trademark: Florisil) having a surface area of more than 100 m$^2$/g and micropore size of 5 Å or more as a catalyst was used. As a result, nitrobenzene at a yield of more than 99% was obtained.

EXAMPLE 8

The same procedure as described in Example 1 was carried out, except that Zeolite (trademark: MCM) as a catalyst was used. As a result, nitrobenzene at a yield of more than 99% was obtained.

EXAMPLE 9

The same procedure as described in Example 1 was carried out. except that a silicious earth as a catalyst was used. As a result, nitrobenzene at a yield of more than 99% was obtained.

EXAMPLE 10

The same procedure as described in Example 1 was carried out, except that Zeolite, sodium mordenite (Na mordenite) as a catalyst was used. As a result, nitrobenzene at a yield of more than 99% was obtained.

EXAMPLE 11

The same procedure as described in Example 1 was carried out, except that Zeolite, NaY as a catalyst was used. As a result, nitrobenzene at a yield of more than 99% was obtained.

EXAMPLE 12

The same procedure as described in Example 1 was carried out, except that Kaoline (available from Hadong, Kyungnam, Korea) as a catalyst was used. As a result, nitrobenzene at a yield of more than 99% was obtained.

EXAMPLE 13

The same procedure as described in Example 1 was carried out, except that Kaoline (available from Hoengchun, Kyungnam, Korea) as a catalyst was used. As a result, nitrobenzene at a yield of more than 99% was obtained.

COMPARATIVE EXAMPLE 1

The same procedure as described in Example 1 was carried out, except that α-alumina having a surface area of 10 to 30 m$^2$/g as a catalyst was used. As a result, nitrobenzene at a yield of 5% was obtained.

COMPARATIVE EXAMPLE 2

The same procedure as described in Example 1 was carried out, except that pearlite as a catalyst was used. As a result, nitrobenzene at a yield of 5% was obtained.

COMPARATIVE EXAMPLE 3

The same procedure as described in Example 1 was carried out, except that sand as a catalyst was used. As a result, nitrobenzene at a yield of 5% was obtained.

COMPARATIVE EXAMPLE 4

The same procedure as described in Example 1 was carried out, except that Kieselguhr (trademark: Celite) having a surface area of about 20 m$^2$/g as a catalyst was used. As a result, nitrobenzene at a yield of 5% was obtained.

COMPARATIVE EXAMPLE 5

The same procedure as described in Example 1 was carried out, except that Molecular sieve having a micropore size of 4 Å as a catalyst was used. As a result, nitrobenzene at a yield of 5% was obtained.

EXAMPLE 14

0.1 mol of toluene, 2 g of silica gel (14–20 mesh) and 0.2 mol of liquid nitrogen dioxide were poured into an autoclave. Next, oxygen was injected at a pressure of 40 psi and then the mixtures were reacted at 45° C. for 1.5 hours while the same level of pressure was maintained. After the completion of the reaction, analysis by gas chromatography revealed the obtainment of nitrobenzene at a yield of more than 99%.

EXAMPLE 15

0.1 mol of chlorobenzene, 2 g of silica gel (14–20 mesh) and 0.2 mol of liquid nitrogen dioxide were poured into an autoclave. Next, oxygen was injected at a pressure of 40 psi and then the mixtures were reacted at 45° C. for 1.5 hours while the same level of pressure was maintained. After the completion of the reaction, analysis by gas chromatography revealed the attainment of nitrobenzene at a yield of more than 99%.

EXAMPLE 16

0.2 mol of toluene, 4 g of silica gel (14–20 mesh) and 0.9 mol of liquid nitrogen dioxide were poured into an autoclave. Next, oxygen was injected at a pressure of 88 psi and then the reactants were reacted at 60° C. for 5 hours while the same level of pressure was maintained. After the completion of the reaction, analysis by gas chromatography revealed the attainment of dinitration reaction at a yield of 93%.

COMPARATIVE EXAMPLE 6

0.2 mol of benzene, 2 g of silica gel (14–20 mesh) and 0.9 mol of liquid nitrogen dioxide were poured into an autoclave. Next, oxygen was injected at a pressure of 120 psi and then the reactants were reacted at 70° C. for 5 hours while the same level of pressure was maintained. After the completion of the reaction, analysis by gas chromatography revealed the attainment of dinitration reaction at a yield of 28%.

COMPARATIVE EXAMPLE 7

After supplying 0.2 mol of benzene and 0.02 mol of ferric chloride to an autoclave, 0.9 mol of liquid nitrogen dioxide was added to the autoclave. Next, oxygen was injected at a pressure of 120 psi and then the reactants were reacted for 6 hours at 70° C. while the same level of pressure was maintained. After the completion of the reaction, dinitrobenzene having a ratio of meta:ortho:para isomers=85:12:3 was obtained at a yield of more than 98% analyzed by gas chromatography.

COMPARATIVE EXAMPLE 8

The same procedure as described in Example 17 was carried out, except that 0.01 mol of ferric chloride and 1.0 mol of liquid nitrogen dioxide were used. After the completion of the reaction, dinitrobenzene having a ratio of meta:ortho:para isomers=85:12:3 was obtained at a yield of more than 98% analyzed by gas chromatography.

COMPARATIVE EXAMPLE 9

After supplying 0.2 mol of toluene and 0.002 mol of ferric chloride to an autoclave, 0.9 mol of liquid nitrogen dioxide was added to the autoclave. Next, oxygen was injected at a pressure of 120 psi. At first the reactants were reacted at room temperature. After 30 minutes, the autoclave was heated to 60° C. and then the reactants were reacted for 3 hours. After the initial 30 minutes, all of toluene was converted into o-nitrotoluene and p-nitrotoluene at a ratio of 55:45, respectively. After 3 hours, 2,4-dinitro-toluene and 2,6-dinitrotoluene (83:17) were formed at a yield of more than 98% analyzed by gas chromatography.

EXAMPLE 17

A catalyst containing ferric ion was prepared as follows. 34 g of ferric chloride was dissolved in 100 ml of water and 25 ml of ethanol. To this, 12.5 g of silica gel (70–230 mesh, for column chromatography) was added and refluxed for 10 hours. After filtrating the solution, the catalyst was washed using water and nitric acid, and baked at 400° C. The same procedure as described in Example 1 was carried out, except that the reaction temperature was 30° C. and the reaction time 2.0 hours. After the completion of the reaction, nitrobenzene was obtained at a yield of more than 96% analyzed by gas chromatography.

Although the present invention has been described in terms of the preferred examples and comparative examples, it will be understood that various modifications and changes will be apparent to and can be readily made by those skilled in the art without departing from the scope and spirit of this invention. For example, catalysts to be used in the present invention are not limited to those described in the above examples, but all those satisfying the conditions of micropore size and surface area are included within the scope of the present invention. Accordingly, it will be obvious that the catalysts such as silicious earth, Kaoline and others satisfy the conditions of micropore size and surface area of the present invention.

In accordance with the nitration process of aromatic compounds of the present invention, mixed acid or nitric acid are not used, so that the spent wast acid is not generated. Further, reactivity is higher, the process is more stable and the recovery of catalysts is easier than in prior art nitration processes.

What is claimed is:

1. A process for nitration of aromatic compounds using a non-acid type nitration process comprising the steps of:
   a) pouring an aromatic compound into an autoclave, then adding nitrogen dioxide and an inorganic oxide type catalyst having a surface area of more than 100 m$^2$/g and a micropore size of more than 5 Å; and
   b) feeding oxygen into the autoclave and conducting a mononitration or dinitration reaction with pressure.

2. The process according to claim 1, wherein said catalyst is insoluble in an organic solvent.

3. The process according to claim 2, wherein said catalyst is selected from the group consisting of silica gel, γ-alumina, magnesium silicate, Zeolite, Kaoline and silicious earth.

4. The process according to claim 3, wherein the Zeolite is meso-porous zeolite, sodium mordenite or NaY.

5. The process according to claim 3, wherein the Zeolite is Zeolite X or Y.

6. The process according to claim 1, wherein said catalyst contains metal ions.

7. The process according to claim 1, wherein said oxygen is pressurized to more than 1 atm depending on the reactivity of the substrate.

8. The process according to claim 7, wherein said oxygen is pressurized to specifically 3 to 8 atm for benzene or toluene.

9. The process according to claim 1, wherein said nitration of aromatic compounds is conducted without additional solvents.

10. The process according to claim 1, wherein said process is followed by the steps of;
    a) filtrating and recovering the catalyst from the reaction mixture; and
    b) adding water to remove nitric acid formed as a by-product by layer-separation.

* * * * *